(12) United States Patent
Lecomte et al.

(10) Patent No.: US 6,919,093 B2
(45) Date of Patent: Jul. 19, 2005

US006919093B2

(54) FORMULATION

(75) Inventors: Jeanne-Marie Lecomte, Paris (FR); Jean-Charles Schwartz, Paris (FR)

(73) Assignee: Bioprojet, Paris (FR)

( * ) Notice: Subject to any disclaimer, the term of this patent is extended or adjusted under 35 U.S.C. 154(b) by 102 days.

(21) Appl. No.: 10/347,332

(22) Filed: Jan. 13, 2003

(65) Prior Publication Data

US 2003/0166718 A1 Sep. 4, 2003

Related U.S. Application Data

(63) Continuation of application No. PCT/EP01/07086, filed on Jun. 22, 2001.

(30) Foreign Application Priority Data

Jun. 23, 2000 (EP) .............................................. 00401799

(51) Int. Cl.[7] .............................. A61K 9/14; A61K 9/16
(52) U.S. Cl. ........................................ 424/489; 424/490
(58) Field of Search ................................ 424/489, 490, 424/493

(56) References Cited

U.S. PATENT DOCUMENTS

| | | | | |
|---|---|---|---|---|
| 4,513,009 A | * | 4/1985 | Roques et al. | |
| 5,679,376 A | * | 10/1997 | Stevens et al. | |
| 5,914,132 A | * | 6/1999 | Kelm et al. | |
| 6,270,804 B1 | * | 8/2001 | Getz et al. | |
| 6,649,186 B1 | * | 11/2003 | Robinson et al. | |

* cited by examiner

*Primary Examiner*—Thurman K. Page
*Assistant Examiner*—Humera N. Sheikh
(74) *Attorney, Agent, or Firm*—Frommer Lawrence & Haug LLP; William S. Frommer; Thomas J. Kowalski

(57) ABSTRACT

A dry powder granulated formulation of the compound racedotril and its use in therapy in the treatment of diarrhoea.

13 Claims, No Drawings

FORMULATION

This is a continuation of PCT/EP01/07086, field Jun. 22, 2001.

The present invention relates to a novel formulation of the compound racecadotril, and its use in the treatment of diarrhoea, in particular in paediatric patients.

Racecadotril, is the compound of structure (I) in the form of a racemate.

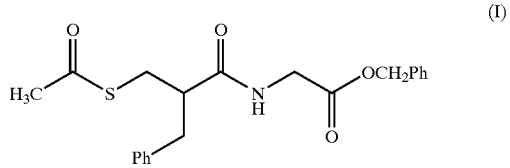

(I)

The compound is generically and specifically disclosed in EP 038758 B1 (equivalent to U.S. Pat. No. 4,513,009) and is indicated to have inter alia, enkephalinase inhibiting and anti-diarrhoea activity. These patents indicate that the compounds may be administered to humans by the oral, parenteral or rectal route, but no details of specific formulations of the claimed compounds is provided. Furthermore, a number of test results are provided indicating the biological activity of the compounds, but in all cases, reference is made only to intravenous formulations of compound.

In seeking to provide suitable formulations for administration to patients it is important to ensure that the formulations are in the most acceptable form to the patient, for example in terms of the nature and appearance of the dosage form, and the ease of ingestion. These features are important in providing a formulation which assists in ensuring patient compliance with the desired dosing regimen. When considering dosage forms for paediatric patients (that is to say children of age 14 or under) the dosage form is particularly critical in ensuring patient compliance. For example, children may often find difficulties in swallowing a tablet or capsule formulation, with the result that liquid or suspension formulations are generally more desirable and are often regarded as the formulation of choice for paediatric patients.

In respect of the present invention, the compound racecadotril is on the market in a number of countries for adult use in the form of a capsule filled with dry powder formulation (and sold as TIORFAN—a trademark of Société Civile de Recherche Bioprojet), but to date a suitable paediatric form (for example a liquid or suspension formulation) has not been provided due to inherent difficulties in formulating the compound. More particularly, the compound is very hydrophobic, ie. water hating, and as such is not readily formulated into a suspension for paediatric use. As noted above, tablets and capsules are not regarded as preferred dosage forms for children, especially younger children for whom a liquid/suspension form is generally regarded as more acceptable.

In order to overcome the problem of providing a suitable paediatric dosage form, Applicants have found racecadotril can be formulated into a dry powder form which can be provided for direct dosing to the patient, or added, for example to food and then ingested by the patient.

The present invention therefore provides, in a first aspect, a dry powder pharmaceutical composition suitable for oral use, comprising racecadotril and a pharmaceutically acceptable carrier.

Suitably, the dry powder composition comprises granules of racecadotril. Granules of racecadotril can be prepared to the desired particle size by standard granulation techniques as described hereinafter in the examples. Typically, the racecadotril granules are prepared and coated with a coating to assist in taste masking of the composition, and then blended with sweetening/flavouring agents to provide the final composition.

Suitably, the granules of racecadotril comprise racecadotril together with a sweetening agent to assist in taste masking of the final composition. Suitable sweetening agents include for example aspartame and sucrose, preferably sucrose. The granules of racecadotril and sucrose, are then coated to assist further with the taste masking of the final product. Film coating of the granules can be achieved using standard techniques. Suitable coatings include for example hydroxypropyl cellulose, acrylate and/or methacrylate co-polymers, resins etc. Preferably, the coating is a polymeric acrylate or methacrylate compound, most preferably EUDRAGIT NE 30D manufactured by ROHM GIMBH & CO. The coated granules of racecadotril can then optionally be further blended with a lubricant to improve powder flow, and further taste masking or sweetening agents to improve palatability to produce the final composition.

Suitable lubricants will be apparent to those skilled in the art, and include for example, long chain fatty acids such as stearic acid and salts thereof, in particular group II metal salts such as magnesium or calcium, or anhydrous colloidal silica. Either a single lubricant or combination of lubricants can be used to achieve the desired flow characteristics. Preferred in the present invention is a single diluent, most preferably anhydrous colloidal silica.

Suitable sweetening and flavouring agents will again be apparent to the skilled person, and include for example sucrose or aspartame as sweeteners, and standard fruit flavouring agents.

It is generally necessary to mill and sieve the granulate to obtain a suitable size fraction. In particular, a particle size from 0.630 to 1.58 is preferred, most preferred the particles are milled and sieved to a fraction size of nearly 1.01 mm.

The dry powder formulations of the present invention are preferably provided in the unit dosage formulation for administration to patients. Suitably, unit dosages comprise from 1 to 50 mg of racecadotril, more suitably 5 to 30 mg of racecadotril. Preferably, unit dosages comprise 6, 10, 18 or 30 mg of racecadotril. In a preferred aspect of the present invention, the unit dose of the dry powder composition is provided in a sachet. The individual sachets ensure the composition is retained dry prior to use, and provide a convenient form form which to dispense the powder.

The dry powder of the present invention can be ingested direct by the patient ie. direct into the patients mouth, or sprinkled onto food prior to ingestion. In addition even though the granules do not form a suspension due to the hydrophobic nature of racecadotril, the powder may also be added to a small amount of clean water prior to administration, ensuring that the water and granules are stirred together vigorously and then provided to the patient before the granules have settled to the bottom of the glass.

As hereinbefore indicated the present composition in particular is advantageous for dosages to paediatric patients, since the only current known formulation is a capsule, and as such not preferred for administration to children, in particular, young children. The present composition of a palatable powder is far more acceptable and effective, either via the direct route into the patient's mouth, or for example sprinkled onto food.

The examples serve to illustrate the invention, but should not be regarded as limiting its scope.

EXAMPLES

1. Preparation of a 250 kg batch of dry powder formulation of racecadotril for subsequent filling onto sachets.

| Component | Percentage (%) | Amount (kg) |
| --- | --- | --- |
| Racecadotril | 1.00 | 2.50 |
| Sucrose | 96.65 | 241.625 |
| Eudragit NE 30D* (as dry weight) | 0.15 | 0.375 |
| Apricot flavouring | 2.00 | 5.000 |
| Colloidal silica | 0.20 | 0.500 |
| Purified water | | 1.250 |

*equivalent to 1.250 kg of solution for a 250 kg batch size

The racecadotril and 10% of the sucrose awere mixed together on a Fielder type granulating mixer for 10 minutes.

The Eudragit was dissolved in purified water and mixed to obtain a homogenous dispersion, then added to the racecadotril/sucrose mixture to form the granules. The granules so formed were then dried in an air-fluidised bed dryer (such as a Franco Moran or Aeromatic type of drier), with a drying temperatre of between 45 and 55 C. until granules were obtained with a moisture content of less than 1%. The dry granules were then mixed with the remainder of the sucrose, the colloidal silica and the flavouring in a mixer (such as a Robotianer inverting type of mixer) and then sized on a Frewitt type oscillating granulator equipped with a screen mesh of aperture 1.01 mm. The resulting sized mixture was then mixed again in a Robotainer inverting container mixer until homogenous.

The final granule containing 1% of active principle is packaged in a sachet dosage strength of from 6–30 mg racecadotril, by filling sachets with 0.6 g/sachet to 3.0 g/sachet of final granule.

What is claimed is:

1. An oral dry powder racecadotril formulation comprising coated granules of racecadotril mixed with a lubricant selected from the group consisting of anhydrous colloidal silica, long chain fatty acids, and salts thereof.

2. The oral dry racecadotril formulation of claim 1 wherein the granules are coated with polymeric acrylate or methacrylate.

3. The oral dry racecadotril formulation of claim 1 wherein the granules are coated with EUDRAGIT NE 30D.

4. The oral dry racecadotril formulation of claim 1 further comprising a sweetening agent.

5. The oral dry racecadotril formulation of claim 2 further comprising a sweetening agent.

6. The oral dry racecadotril formulation of claim 3 further comprising a sweetening agent.

7. The oral dry racecadotril formulation of claim 4 further comprising a flavoring agent.

8. A method of treating diarrhea in a mammal comprising orally administering the oral dry racecadotril formulation of any one of claims 1 to 7.

9. The method of claim 8 comprising sprinkling the oral dry racecadotril formulation onto food and ingesting the food.

10. The oral dry racecadotil formulation of claim 1 in a unit dose form of 1 to 50 mg of racecadotril.

11. The oral dry racecadotil formulation of claim 1 in a unit dose form of 5 to 30 mg of racecadotril.

12. The oral dry racecadotril formulation of claim 11 comprising 6, 10, 18 or 30mg of racecadotril.

13. A unit dose of racecadotril comprising the oral dry formulation of claim 1 packaged in a sachet.

* * * * *

UNITED STATES PATENT AND TRADEMARK OFFICE
CERTIFICATE OF CORRECTION

PATENT NO.    : 6,919,093 B2
DATED         : July 19, 2005
INVENTOR(S)   : Jeanne-Marie Lecomte et al.

It is certified that error appears in the above-identified patent and that said Letters Patent is hereby corrected as shown below:

<u>Title page,</u>
Item [57], ABSTRACT,
Line 2, delete "racedotril" and insert -- racecadotril --.

Signed and Sealed this

Fifteenth Day of November, 2005

JON W. DUDAS
*Director of the United States Patent and Trademark Office*